United States Patent
Tarur et al.

(10) Patent No.: US 7,678,912 B2
(45) Date of Patent: Mar. 16, 2010

(54) PROCESS FOR PREPARATION OF 4-AMINO-1-ISOBUTYL-1H-IMIDAZO[4,5-C]-QUINOLINE (IMIQUIMOD)

(75) Inventors: Venkatasubramanian Radhakrishnan Tarur, Mumbai (IN); Suresh Mahadev Kadam, Navi Mumbai (IN); Anil Purushottam Joshi, Thane (IN); Sachin Baban Gavhane, Ahmednagar (IN)

(73) Assignee: USV, Ltd., Mumbai (IN)

( * ) Notice: Subject to any disclaimer, the term of this patent is extended or adjusted under 35 U.S.C. 154(b) by 57 days.

(21) Appl. No.: 11/575,927

(22) PCT Filed: Dec. 27, 2004

(86) PCT No.: PCT/IN2004/000411

§ 371 (c)(1),
(2), (4) Date: Mar. 23, 2007

(87) PCT Pub. No.: WO2006/070379

PCT Pub. Date: Jul. 6, 2006

(65) Prior Publication Data

US 2008/0058527 A1    Mar. 6, 2008

(51) Int. Cl.
*C07D 215/00* (2006.01)
(52) U.S. Cl. .................................................. 546/157
(58) Field of Classification Search .................. 546/157
See application file for complete search history.

(56) References Cited

U.S. PATENT DOCUMENTS 4,689,338 A * 8/1987 Gerster ........................ 514/293
6,852,861 B2 * 2/2005 Merli et al. .................... 546/82

OTHER PUBLICATIONS

Noriaki Minakawa et al., "New Base Pairing Motifs. The Synthesis and Thermal Stability of Oligodeoxynuclueotides Containing Imidazopyridopyrimidine Nucleosides with the Ability to Form Four Hydrogen Bonds," Journal of the American Chemical Society, 2003.

* cited by examiner

*Primary Examiner*—D. Margaret Seaman
*Assistant Examiner*—Nizal S Chandrakumar
(74) *Attorney, Agent, or Firm*—Pharmaceutical Patent Atty's, LLC

(57) ABSTRACT

A process for preparation of 1-isobutyl-1H-imidazo-[4,5-c]-quinoline-5-N-oxide, comprising oxidation of 1-isobutyl-1H-imidazoquinoline with meta-chloroperbenzoic acid.

16 Claims, No Drawings

PROCESS FOR PREPARATION OF 4-AMINO-1-ISOBUTYL-1H-IMIDAZO[4,5-C]-QUINOLINE (IMIQUIMOD)

TECHNICAL FIELD OF THE INVENTION

The present invention relates to a process for synthesis of 4-Amino-1-isobutyl-1H-imidazo[4,5-c]-quinoline. The invention also relates to a novel purification method via a novel maleate salt.

BACKGROUND OF THE INVENTION

Imiquimod, 4-Amino-1-isobutyl-1H-imidazo-[4,5-c]-quinoline (VIII) is an immune response modifier, useful for treating viral infections such as genital warts. Imiquimod is disclosed in U.S. Pat. Nos. 4,689,338 and 5,238,944 and has the structure (VIII).

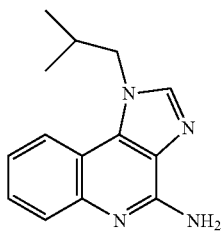

(VIII)

Several methods are known in the prior art for making Imiquimod (VIII).

The process of converting 1-Isobutyl-1H-imidazo-[4,5-c]-quinoline (II) to 1-Isobutyl-1H-imidazo-[4,5-c]-quinoline-5-N-oxide (III) has been disclosed in WO 2004/0011462 A1, WO 2004/009593 A1 using peracetic acid in toluene as a solvent. This conversion is also reported in WO 92/15581, WO 9206093 and U.S. Pat. No. 5,175,296 using a combination of formic acid and peracetic acid. However, since the yields are poor and reaction being incomplete there is a need to develop an oxidation process with milder conditions.

Reported prior arts describe various methods for the preparation of 4-Amino-1-isobutyl-1H-imidazo[4,5-c]quinoline (VIII) i.e. Imiquimod wherein the Introduction of amino function in the 4-position is described in three ways. Nucleophilic substitution of a leaving group e.g. Cl or triflate with ammonia, dibenzylamine or an azido group is the first method. The second, is by reacting 1-Isobutyl-1H-imidazo-[4,5-c]-quinoline-5-N-oxide (III) with ammonium hydroxide or its salts in presence of tosylchloride at 0-5° C. The third reported method is by reacting 1-Isobutyl-1H-imidazo-[4,5-c]-quinoline-5-N-oxide with benzoyl isocyanate.

Patents WO 2004/009593, WO 92/06093 and U.S. Pat. Nos. 5,395,937; 5,756,747; 4,988,815; 5,602,256; 5,578,727; 4,698,348; 4,689,388 as well as European patents EP 145340, EP 0385630, EP 310950 and JP 04193866 and examples therein, describe nucleophilic substitution reactions.

In WO 97/48704 the amino group is introduced by reaction of a 4-Chloro derivative with Sodium azide to obtain a tetrazole moiety. Treatment of the tetrazole moiety with triphenyl phosphine gives the 4-amino derivative.

In U.S. Pat. No. 5,395,937 a 4-triflate derivative reacts with dibenzylamine to give 4-dibenzylamino derivative. Subsequent catalytic reduction gives the desired amino function in 4-position.

U.S. Pat. No. 5,756,747 discloses the nucleophilic substitution with ammonia on the corresponding 4-chloro derivative, which is prepared by isomerization of 1-Isobutyl-1H-imidazo-[4,5-c]-quinoline-5-N-oxide (III) via the 4-hydroxy derivative followed by reaction with $POCl_3$. Several patents disclose nucleophilic substitution of 4-Chloro-1-isobutyl-1H-imidazo-[4,5-c]-quinoline (V) with ammonia at high temperature and high pressure. These include U.S. Pat. No. 4,988,815; U.S. Pat. No. 5,602,256; U.S. Pat. No. 5,578,727; U.S. Pat. No. 4,698,348; U.S. Pat. No. 4,689,388; EP 145340; EP 0385630; EP 310950 and JP 04193866.

The patents WO 2004/009593, US2004138459, disclose a process for the preparation of 4-Amino-1-isobutyl-1H-imidazo-[4,5-c]-quinoline (VIII) (i.e. Imiquimod) by introducing an amino group in the 4-position via 1-Isobutyl-1H-imidazo-[4,5-c]-quinoline-4-phthalimide intermediate (i.e. phthalimido protecting group).

WO 92/06093 discloses reaction of 1-Isobutyl-1H-imidazo-[4,5-c]-quinoline-5-N-oxide (III) with ammonium hydroxide or ammonium salts in the presence of tosyl chloride at 0 to 5° C. to give Imiquimod.

WO 92/15581 relates to reaction of 1-Isobutyl-1H-imidazo-[4,5-c]-quinoline-5-N-oxide (III) with benzoyl isocyanate which on subsequent hydrolysis yields Imiquimod (VIII).

Purification of Imiquimod has been described via formation of pharmaceutical salts in WO 2004/009593, U.S. Pat. No. 4,689,338 i.e. using HCl, $H_2SO_4$, $H_3PO_4$, $HNO_3$ and Methane sulfonic acid. There is still a need for preparation of 4-Amino-1-isobutyl-1H-imidazo-[4,5-c]-quinoline (VIII) namely Imiquimod in high yield and purity.

OBJECTIVES

An object of the present invention is to develop a simple process for the preparation of Imiquimod.

Another object of the present invention is to provide a purification process, which is simple and implemented on a large scale.

Further object of the present invention is to produce Imiquimod (VIII) of high purity.

SUMMARY OF THE INVENTION

The present invention provides a process for preparing 4-Amino-1-isobutyl-1H-imidazo-[4,5-c]-quinoline (VIII) comprising:

1) Reacting 1-Isobutyl-1H-imidazo-[4,5-c]-quinoline (II) with per acids preferably meta-chloro perbenzoic acid in organic solvent substantially affording cleaner 1-Isobutyl-1H-imidazo-[4,5-c]-quinoline-5-N-oxide (III). This is further purified as its hydrochloric salt (IV).
2) Conversion of 5-N-oxide hydrochloride (IV) to the 4-chloro derivative (V) by treating with phosphorous oxychloride.
3) In another aspect of the present invention is directed to a process for preparing 4-amino-1H-imidazo-[4,5-c]-quinoline (VIII) by reacting a compound of [4-Chloro-1H-imidazo-[4,5-c]-quinoline (V)] with an alkali halide preferably sodium iodide to produce the corresponding 4-iodo derivative (VI) which is converted to (VIII) by treatment with ammonia.
4) Isolating the product VIII as a pharmaceutically acceptable maleate salt (VII).
5) Finally converting the Imiquimod maleate (VII) to Imiquimod (VIII) in methanolic ammonia having purity greater than 99.5% by HPLC.

DETAILED DESCRIPTION OF INVENTION

These and other aspects of the present invention will now be described in more detail with reference to the following detailed description of the invention.

The present invention relates to a process for preparing Imiquimod, 4-Amino-1-isobutyl-1H-imidazo-[4,5-c]-quinoline of formula (VIII). However, the inventive process can be used to prepare any compound within the scope of formula (VIII) and its derivative including those disclosed in U.S. Pat. Nos. 5,756,747; 5,395,937; 4,689,338; EP 385630, WO 97/48704; WO 92/06093 and WO 92/15581 all of which are incorporated by reference in their entirety.

The cyclisation of 3-Amino-4-(isobutylamino)-quinoline (I) is accomplished by treating it with formic acid to obtain 1-isobutyl-1H-imidazo-[4,5-c]-quinoline (II). Satisfactory yield by any method known in the art including those disclosed in patents WO 92/06093 and U.S. Pat. No. 5,175,296 all of which are incorporated by reference in their entirety.

The 4-Iodo-1-isobutyl-1H-imidazo-[4,5-c]-quinoline i.e. (VI) is prepared by reaction of 4-Chloro-1-isobutyl-1H-imidazo-[4,5-c]-quinoline (V) with alkali halide such as Sodium iodide.

The 1-Isobutyl-1H-imidazo-[4,5-c]-quinoline-5-N-oxide of formula (III) can be obtained by any method known in the art including those in U.S. Pat. No. 5,756,747; WO 92/06093 and WO 92/15581 all of which are incorporated by reference in their entirety. Here it has been achieved using meta-chloroperbenzoic acid. A preferred solvent is an aliphatic alkyl ester where in carbon chain may be preferably $C_1$-$C_4$. Preferably Ethyl acetate is used as solvent. The reaction is preferably carried out at a temperature of between 20 to 80° C. more preferably between 40 to 80° C. and most preferably at about 70° C. The meta-chloroperbenzoic acid is preferably added over a period of about 1 to 3 hrs more preferably from about 1 to 2 hrs and most preferably for about 1 hr and 30 min. The reaction is complete when no 1-Isobutyl-1H-imidazo-[4,5-c]-quinoline (II) is detected by TLC. When the reaction is complete this excess of m-chloro benzoic acid is filtered and the organic layer containing the 1H-Imidazo-[4,5-c]-quinoline-5-N-oxide (III) compound is washed with ethyl acetate and further concentrated. This reaction is very clean and gives higher yields in comparison to reported reference disclosed in patent WO 2004/011462 A1, WO 2004/009593 A1, WO 92/15581, WO 9206093, U.S. Pat. No. 5,175,296.

The 1-Isobutyl-1H-imidazo-[4,5-c]-quinoline-5-N-oxide (III) is purified by preparing its hydrochloride salt (IV) in 8% alcoholic hydrochloride solution. A preferred alcohol is from C1-C4 aliphatic alcohol. Most preferably ethanol is used. The hydrochloride formation is carried out at a temperature between 5 to 20° C., more preferably between 10 to 20° C. and most preferably between 10 to 15° C. When the hydrochloride formation is complete the product (IV) is filtered and washed with ethyl alcohol.

The 4-Chloro-1H-imidazo-[4,5-c]-quinoline an intermediate of formula (V) is obtained by reaction of 1H-imidazo-[4,5-c]-quinoline-5-N-oxide hydrochloride of formula (IV) with phosphorous oxychloride in an aprotic solvent i.e. dimethylformamide by any method known in the art including those disclosed in U.S. Pat. No. 4,689,338 all of which are incorporated by reference in their entirety herein.

The 4-Iodo-1H-imidazo-[4,5-c]-quinoline (VI), a novel intermediate is prepared by reacting 4-Chloro-1H-imidazo-[4,5-c]-quinoline-(V) in an aliphatic ketone preferably alkali halide via the halogen exchange reaction. The reaction is preferably carried out in the presence of sodium iodide. The reaction is achieved in acetone as a solvent. The reaction is preferably carried out at temperatures between 25 to 35° C. over a period of about 8-10 hrs. This novel compound is characterized by its M.P., $^1$H NMR and mass spectroscopy.

In the penultimate stage, 4-Iodo-1H-imidazo-[4,5-c]-quinoline (VI) is converted to Imiquimod (Crude), which is purified via its maleate salt (VII) to provide a compound of invention of formula (VIII). The reaction is carried out in the presence of ammonium hydroxide or preferably ammonia.

Imiquimod (Crude) is subsequently converted to its pharmaceutically acceptable maleate salt (VII) in aqueous alcohol. The reaction is carried out in aliphatic alcohol and most preferably in methanol. The proportion of alcohol:water is 2:1. The salt formation is preferably done at 60 to 90° C.

SCHEME-I

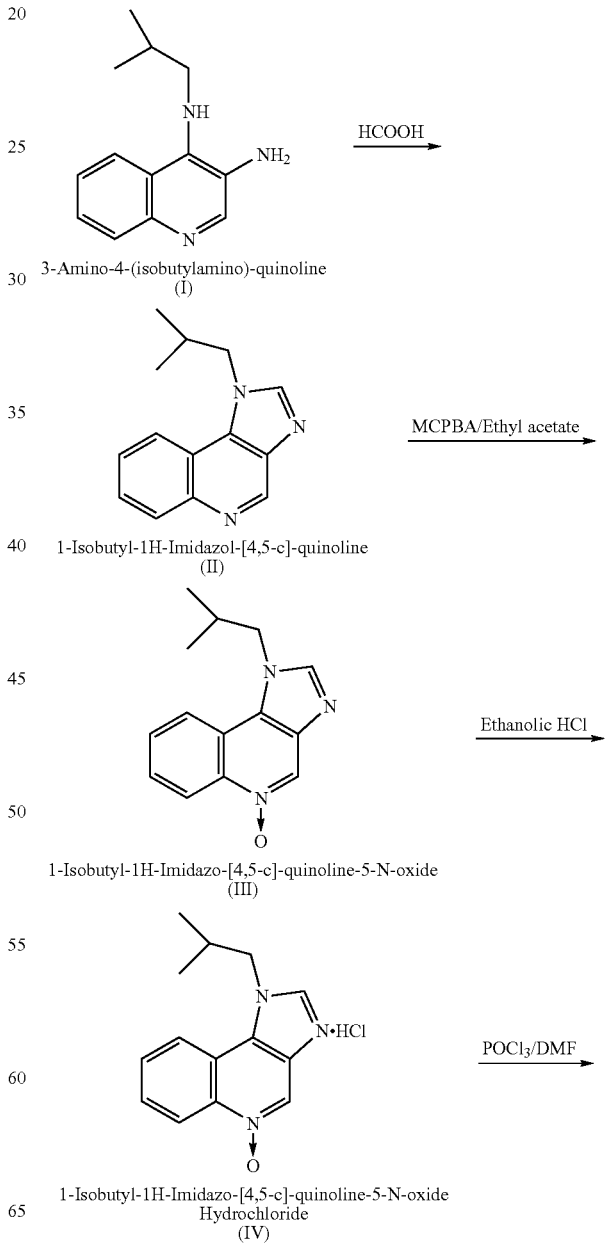

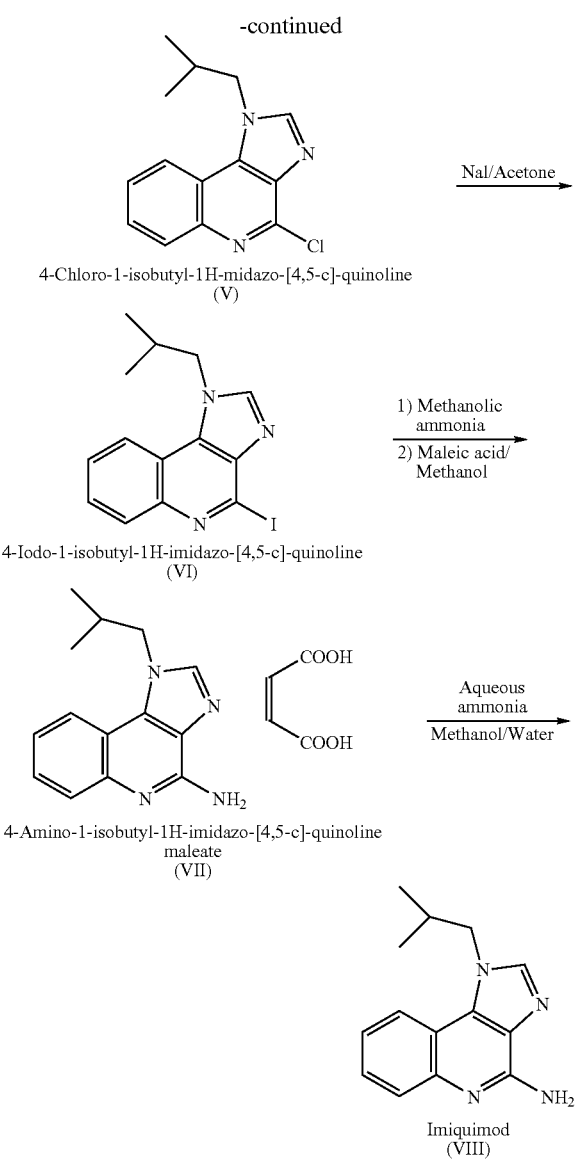

4-Chloro-1-isobutyl-1H-midazo-[4,5-c]-quinoline (V)

NaI/Acetone →

4-Iodo-1-isobutyl-1H-imidazo-[4,5-c]-quinoline (VI)

1) Methanolic ammonia
2) Maleic acid/Methanol

4-Amino-1-isobutyl-1H-imidazo-[4,5-c]-quinoline maleate (VII)

Aqueous ammonia / Methanol/Water →

Imiquimod (VIII)

Maleate formation is completed in 2 to 3 hrs and then reaction mass is cooled slowly to 25 to 35° C., at this point Imiquimod maleate (VII) crystallizes out. The product is isolated by filtration. Imiquimod maleate (VII) is obtained in good yield (~90%) and purity (99% by HPLC). Imiquimod maleate salt (VII) is taken preferably in a mixture of water, methanol and liquor ammonia. The reaction mass is preferably heated to 60 to 80° C. more preferably at 70° C. for neutralization of salt. At an alkaline pH (~9-11) pale white Imiquimod (VIII) precipitates out. The reaction mass is cooled initially to 25 to 30° C. and finally cooled to 8 to 10° C. wherein pure Imiquimod precipitates out. The purity of product enhances from 99 to 99.5% by HPLC.

EXPERIMENTAL DATA

Example No. 1

Preparation of 1-Isobutyl-1H-imidazo-[4,5-c]-quinoline (II)

3-Amino-4-isobutyl amino quinoline (215 gm, 1.0 mole) was dissolved in formic acid (1000 ml) and further refluxed the reaction mass to 110-115° C. Reflux was maintained for 8-10 hrs. After completion of reaction excess formic acid was removed under reduced pressure and 3.5 L of water was added to the concentrated mass. This diluted mass was then basified with 30% NaOH to pH (10 to 11) at 20° C. The reaction mass was further cooled to 10° C. and stirred for further 3 hrs to obtain solid. The solid was filtered, washed with water and dried to get the title compound (221 gm, 98%) as a white solid.

| M.P. | 91 to 94° C. |
|---|---|
| MS-(m/z) | M⁺ 226 |
| ¹HNMR (200 MHz, DMSO D₆) | |
| δ Values | Proton |
| 0.95 | (6H, d, $CH_3 \times 2$) |
| 2.1-2.2 | (1H, m, —CH) |
| 4.5 | (2H, d, $CH_2$) |
| 7.7 | (2H, m, Ar) |
| 8.2-8.3 | (2H, m, Ar) |
| 8.4 | (1H, s, \N—CH=N—/) |
| 9.25 | (1H, s, —C$\underline{H}$=N—) |

Example No. 2

Preparation of 1-Isobutyl-1H-imidazo-[4,5-c]-quinoline-5-N-oxide.HCl (IV)

The compound from Example 1 (220 gm, 0.978 moles) was added to ethyl acetate (1760 ml). The reaction mass was heated to 60 to 65° C. for dissolution. Added meta-chloroperbenzoic acid (485 gm, 70%, 1.377 moles) in lots at 60-65° C. over a period of 2-3 hrs and the temperature was maintained for 6-8 hrs. After completion of reaction, the upper aqueous layer was separated. The lower organic layer was then concentrated under vacuum. To this concentrated mass was added 8% ethanolic hydrochloride (450 ml) at 10-15° C. The hydrochloride salt was precipitated which was filtered, washed with ethyl acetate and dried to obtain the title product (255 gm, 94%).

| M.P. | 200 to 204° C. |
|---|---|
| MS-(m/z) | M⁺ 241 |
| ¹HNMR (200 MHz, DMSO D₆) | |
| δ Values | Proton |
| 0.95 | (6H, d, $CH_3 \times 2$) |
| 2.2-2.5 | (1H, m, —CH) |
| 4.6 | (2H, d, $CH_2$) |
| 8.0-8.1 | (2H, m, Ar) |
| 8.5-8.7 | (2H, m, Ar) |
| 8.85 | (1H, s, —C$\underline{H}$=N—) |
| 10.0 | (1H, s, —CH=N→O) |

Example No. 3

Preparation of 4-Chloro-1-isobutyl-1H-imidazo-[4,5-c]-quinoline (V)

The compound from Example 2 (100 gm; 0.3603 moles) and phosphorous oxychloride (157 gm) were then added to N,N-Dimethylformamide (600 ml) at 20° C. The resulting solution was stirred for 30 minutes at 20° C. and subsequently heated to 80° C. for 2 hrs. The resulting suspension was drowned in the 3.0 L cold water and was basified to pH as 9 to 10 with 30% sodium hydroxide solution. The precipitated solid was filtered, washed with water and dried to obtain the title product (70 gm, 74%).

| M.P. | 134 to 136° C. |
|---|---|
| MS-(m/z) | $M^+$ 261 |
| $^1$HNMR (200 MHz, DMSO $D_6$) | |
| δ Values | Proton |
| 0.95 | (6H, d, $CH_3 \times 2$) |
| 2.17-2.2 | (1H, m, —CH) |
| 4.5 | (2H, d, $CH_2$) |
| 7.7-7.8 | (2H, m, Ar) |
| 8.0-8.3 | (2H, m, Ar) |
| 8.5 | 1H, s, —C$\underline{H}$=N—) |

Example No. 4

Preparation of 4-Iodo-1-isobutyl-1H-Imidazo-[4,5-c]-quinoline (VI)

The compound from Example 3 (50 gm, 0.19 mole) was added to acetone (200 ml). Separately prepared solution of sodium iodide in acetone (i.e. 28 gm in 200 ml acetone) was then added dropwise to the reaction mass and maintained at 25-30° C. for 8 hrs. The precipitated sodium chloride was filtered and the acetone was concentrated under vacuum to obtain the title product.

| M.P. | 125 to 127° C. |
|---|---|
| MS-(m/z) | $M^+$ 351 |
| $^1$HNMR (200 MHz, DMSO $D_6$) | |
| δ Values | Proton |
| 0.93 | (6H, d, $CH_3 \times 2$) |
| 2.1-2.7 | (1H, m, —CH) |
| 4.53-4.57 | (2H, d, $NCH_2$) |
| 7.75-7.8 | (2H, m, Ar) |
| 8.08-8.11 | (1H, m, Ar) |
| 8.33-8.38 | (1H, m, Ar) |
| 8.5 | (1H, s, —C$\underline{H}$=N—) |

Example No. 5

Preparation of Imiquimod (Crude)

The compound from Example 4 (67 gm, 0.1903 mole) was added to 750 ml of 15% methanolic ammonia solution in a pressure reactor (i.e. autoclave) and heated to 150-155° C. (~20 Kg pressure). The reaction mass was then maintained at this temperature, when all the product precipitates out. The precipitated solid was filtered and washed with 50 ml methanol. The product was dried at 55 to 60° C. for 8 hrs to obtain the title product (40 gm, 86%).

Part A

Preparation of 4-Amino-1-isobutyl-1H-Imidazo-[4,5-c]-quinoline maleate salt (VII)

The compound from Example 5 (35 gm, 0.145 mole) was added to mixture of 350 ml of methanol and 175 ml water. Subsequently, 35 gm (0.3017 mole) maleic acid was added in one lot and the reaction mass was heated to reflux temperature 74° C. Charcoalised and maintained the reaction mass for 0.5 hr. Washed the hyflo bed with 20 ml hot methanol and filtered the hot reaction mass through hyflo. The filtrate was then slowly cooled to RT and then to 8-10° C. in 1 hr. The precipitated product was filtered and washed with 20 ml of methanol. The product was dried at 55-60° C. (47.2 gm, 91%).

| M.P. | 190 to 192° C. |
|---|---|
| MS-(m/z) | $M^+$ 241 |
| $^1$HNMR (200 MHz, DMSO $D_6$) | |
| δ Values | Proton |
| 0.95 | (6H, d, $CH_3 \times 2$) |
| 2.1-2.3 | (1H, m, CH) |
| 4.5 | (2H, d, $NCH_2$) |
| 6.09 | (2H, S, =C—H of maleic acid) |
| 7.5-7.8 | (3H, m, Ar) |
| 8.1 | (1H, d, Ar) |
| 8.5 | (1H, s, —C$\underline{H}$=N—) |
| 8.8 | (2H, brs, —$NH_2$) $D_2O$ exchangeable |

Part B

Preparation of 4-Amino-1-isobutyl-1H-Imidazo-[4,5-c]-quinoline (VIII)

The compound from Example 6 (47.2 gm, 0.132 mole) was added to a mixture of 350 ml methanol and 175 ml water. The reaction mass was heated to 75° C. and 3.5 gm charcoal was further added and maintained for 0.5 hr. Filtered the hot reaction mass through hyflo and subsequently added 25% ammonia solution (40 ml) till alkaline pH. Product precipitated out was filtered, washed with water and dried to obtain the title product (31.4 gm, 89.7%).

| M.P. | 292 to 294° C. |
|---|---|
| MS-(m/z) | $M^+$ 241 |
| $^1$HNMR (200 MHz, DMSO $D_6$) | |
| δ Values | Proton |
| 0.97 | (6H, d, $CH_3 \times 2$) |
| 2.18-2.25 | (1H, m, CH) |
| 4.5 | (2H, d, $CH_2$) |
| 7.5-7.72 | (2H, m, Ar) |
| 7.8-7.9 | (2H, m, Ar) |
| 8.5 | (1H, s, —C$\underline{H}$=N—) |
| 8.8 | (1H, s, $NH_2$) $D_2O$ exchangeable |

We claim:

1. In a process of preparation of 4-Amino-1-isobutyl-1H-imidazo-[4,5-c]-quinoline, the improvement comprising:
   Oxidizing 1-Isobutyl-1H-imidazo-[4,5-c]-quinoline with meta-chloroperbenzoic acid in organic solvent to produce 1-Isobutyl-1H-imidazo-[4,5-c]-quinoline-5-N-oxide.

2. A process according to claim 1 wherein said per acid used in oxidation is meta-chloroperbenzoic acid.

3. A process according to claim 1, wherein said organic solvent used in oxidation is ethyl acetate.

4. A process according to claim 3, wherein said oxidation is performed at about 60° C. to 70° C.

5. A process according to claim 4 wherein said oxidation reaction is completed in about 6-10 hrs.

6. A process according to claim 1, wherein said 1-Isobutyl-1H-imidazo-[4,5-c]-quinoline-5-N-oxide is purified in ethanolic hydrochloric acid to produce 1-Isobutyl-1H-imidazo-[4,5-c]-quinoline-5-N-oxide hydrochloride.

7. A process according to claim 6 further comprises converting, said Isobutyl-1H-imidazo-[4,5-c]-quinoline-5-N-oxide hydrochloride to 4-chloro-1-Isobutyl-1H-imidazo-[4,5-c]-quinoline using chlorinating agent.

8. A process according to claim 7, wherein said 4-chloro-1-Isobutyl-1H-imidazo-[4,5-c]-quinoline is reacted with iodide compound in a solvent medium to produce 4-iodo-1-Isobutyl-1H-imidazo-[4,5-c]-quinoline.

9. A process according to claim 8 wherein said iodide compound comprises sodium iodide and said solvent medium comprises acetone.

10. A process according to claim 8 wherein said 4-iodo-1-Isobutyl-1H-imidazo-[4,5-c]-quinoline is converted to 4-amino-1-isobutyl-1H-imidazo-[4,5-c]-quinoline in methanolic ammonia.

11. A process according to claim 10, wherein said conversion is at about 140° C.-155° C. and at about 15-20 Kg pressure.

12. A process according to claim 11, wherein said conversion is completed in about 8 hrs.

13. A process according to claim 10, further comprising purifying said 4-amino-1-Isobutyl-1H-imidazo-[4,5-c]-quinoline from 4-amino-1-isobutyl-1H-imidazo[4,5-c]quinoline maleate in aqueous methanol.

14. A process according to claim 13 wherein the reaction temperature is about 70° C.-80° C.

15. A process according to claim 14 wherein the 4-amino-1-isobutyl-1H-imidazo[4,5-c]quinoline is isolated at about 8-10° C.

16. A process according to claim 15 wherein the 4-amino-1-isobutyl-1H-imidazo[4,5-c]quinoline obtained is greater than 99% in purity.

* * * * *